US00PP16347P2

(12) United States Plant Patent
Smith

(10) Patent No.: US PP16,347 P2
(45) Date of Patent: Mar. 14, 2006

(54) ***CHRYSANTHEMUM* PLANT NAMED 'ROSY YOVICTORIA'**

(50) Latin Name: *Chrysanthemum×morifolium*
Varietal Denomination: Rosy Yovictoria

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 8 days.

(21) Appl. No.: 10/764,867

(22) Filed: Jan. 26, 2004

(51) Int. Cl.
*A01H 5/00* (2006.01)

(52) U.S. Cl. ..... Plt./287

(58) Field of Classification Search ..... Plt./287, Plt./291, 292, 293
See application file for complete search history.

*Primary Examiner*—Howard J. Locker
(74) *Attorney, Agent, or Firm*—C. A. Whealy

(57) ABSTRACT

A new and distinct cultivar of *Chrysanthemum* plant named 'Rosy Yovictoria', characterized by its compact, upright and somewhat outwardly spreading plant habit; freely branching habit; dense and full plant habit; uniform and freely flowering habit; decorative-type inflorescences with elongated oblong-shaped ray florets; red purple-colored ray florets; and natural season flowering in late September in the Northern Hemisphere.

2 Drawing Sheets

Botanical classification/cultivar designation: *Chrysanthemum×morifolium* cultivar Rosy Yovictoria.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Rosy Yovictoria'.

The new cultivar is a product of a planned breeding program conducted by the Inventor in Alva, Fla. The objective of the breeding program is to create new garden-type *Chrysanthemum* cultivars having inflorescences with desirable inflorescence forms, attractive floret colors and good garden performance.

The new *Chrysanthemum* is a naturally-occurring whole plant mutation of the *Chrysanthemum×morifolium* cultivar Yovictoria, disclosed in U.S. Plant Pat. No. 13,799. The new *Chrysanthemum* was discovered and selected by the Inventor as a single flowering plant from within a population of plants of the cultivar Yovictoria in a controlled environment in Alva, Fla. in April, 2002. The selection of this plant was based on its desirable inflorescence form, attractive ray floret color and good garden performance.

Asexual reproduction of the new cultivar by terminal vegetative cuttings in a controlled environment in Alva, Fla. since June, 2002, has shown that the unique features of this new *Chrysanthemum* are stable and reproduced true to type in successive generations.

SUMMARY OF THE INVENTION

The cultivar Rosy Yovictoria has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Rosy Yovictoria'. These characteristics in combination distinguish 'Rosy Yovictoria' as a new and distinct cultivar:

1. Compact, upright and somewhat outwardly spreading plant habit.
2. Freely branching habit; dense and full plants.
3. Uniform and freely flowering habit.
4. Decorative-type inflorescences with elongated oblong-shaped ray florets.
5. Red purple-colored ray florets.
6. Natural season flowering in late September in the Northern Hemisphere.

In side-by-side comparisons conducted in Alva, Fla., plants of the new *Chrysanthemum* differed from plants of the parent, the cultivar Yovictoria, primarily in ray floret coloration as plants of the cultivar Yovictoria had lavender-colored ray florets. In addition, plants of the new *Chrysanthemum* flowered a couple of days later than plants of the cultivar Yovictoria when grown under natural season conditions.

Plants of the new *Chrysanthemum* differ from plants of the cultivar Zesty Yovictoria, disclosed in U.S. Plant Pat. No. 15,323, primarily in ray floret coloration.

Plants of the new *Chrysanthemum* can be compared to plants of the *Chrysanthemum* cultivar Helen, disclosed in U.S. Plant Pat. No. 9,793. In side-by-side comparisons conducted in Alva, Fla., plants of the new *Chrysanthemum* differed from plants of the cultivar Helen in the following characteristics:

1. Plants of the new *Chrysanthemum* were more rounded and mounding than plants of the cultivar Helen.
2. Plants of the new *Chrysanthemum* had smaller inflorescences than plants of the cultivar Helen.
3. Plants of the new *Chrysanthemum* flowered about three days later than plants of the cultivar Helen when grown under natural season conditions.
4. Plants of the new *Chrysanthemum* flowered a few days earlier than plants of the cultivar Helen when grown under artificial short day/long night photoperiodic conditions.

Plants of the new *Chrysanthemum* can also be compared to plants of the *Chrysanthemum* cultivar Savona, not patented. In side-by-side comparisons conducted in Alva, Fla., plants of the new *Chrysanthemum* differed from plants of the cultivar Savona in the following characteristics:

1. Plants of the new *Chrysanthemum* were smaller and more rounded than plants of the cultivar Savona.
2. Plants of the new *Chrysanthemum* flowered about ten days earlier than plants of the cultivar Savona when grown under natural season conditions.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Rosy Yovictoria' grown in a container.

The photograph on the second sheet comprises a close-up view of typical inflorescences of the cultivar 'Rosy Yovictoria'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Alva, Fla. during the winter in a fiberglass-covered greenhouse under conditions and practices which approximate those generally used in commercial garden-type *Chrysanthemum* production. One cutting was planted in a 15.25-cm container in early December, 2002. Plants were pinched one time, that is, the terminal apex was removed to enhance branching, at the end of December. One week after the pinch, plants were exposed to short day/long light photoperiodic treatments until flowering. During the production of the plants, day temperatures averaged 26° C. and night averaged 18° C. Measurements and numerical values represent averages for typical flowering plants.

Botanical classification: *Chrysanthemum×morifolium* cultivar Rosy Yovictoria.

Commercial classification: Decorative-type garden *Chrysanthemum*.

Parentage: Naturally-occurring whole plant mutation of the *Chrysanthemum×morifolium* cultivar Yovictoria, disclosed in U.S. Plant Pat. No. 13,799.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with mounded crown. Stems initially upright, then somewhat outwardly spreading; compact growth habit. Freely branching with lateral branches potentially forming at every node. Moderately vigorous.

*Plant height.*—About 17 cm.

*Plant diameter.*—About 26.5 cm.

*Lateral branches.*—Length: About 15.5 cm. Diameter: About 2.75 mm. Internode length: About 1 cm. Aspect: Upright and outwardly spreading. Texture: Pubescent. Color: 144A to 146A.

*Foliage description.*—Leaf arrangement: Alternate. Length: About 5.2 cm. Width: About 4.1 cm. Apex: Cuspidate to mucronate. Base: Truncate. Margin: Palmately lobed, sinuses divergent. Texture, upper surface: Slightly pubescent. Texture, lower surface: Pubescent; veins prominent. Color: Developing and fully expanded foliage, upper surface: 147A. Developing and fully expanded foliage, lower surface: Darker than 147B. Venation, upper surface: 147A. Venation, lower surface: Close to 147B. Petiole length: About 1.6 cm. Petiole diameter: About 2.5 mm. Petiole color, upper surface: 147A to 147B. Petiole color, lower surface: 147B.

Inflorescence description:

*Appearance.*—Decorative-type inflorescence form with elongated oblong-shaped ray florets. Inflorescences borne on terminals above foliage, arising from leaf axils. Ray florets developing acropetally on a capitulum. About nine inflorescences per lateral branch.

*Flowering response.*—Under natural season conditions, plants flower in late September in the Northern Hemisphere.

*Inflorescence bud (before showing color).*—Height: About 4 mm. Diameter: About 6 mm. Shape: Oblate. Color (lower surface of phyllaries): Close to 147A.

*Inflorescence size.*—Diameter: About 3.4 cm. Depth (height): About 1.2 cm. Disc diameter: No disc florets observed. Receptacle diameter: About 2 mm.

*Ray florets.*—Shape: Elongated oblong. Length: About 1.6 cm. Corolla tube length: About 3.5 mm. Width: About 5.5 mm. Apex: Emarginate. Margin: Fused. Texture: Smooth, glabrous; satiny. Surface: Mostly flat. Orientation: Initially upright, then perpendicular to vertical. Number of ray florets per inflorescence: About 87 in numerous whorls. Color: When opening and fully opened, upper surface: Close to 9D overlain with close to 60A. When opening and fully opened, lower surface: Close to 11D faintly underlain with close to 60A.

*Disc florets.*—None observed.

*Phyllaries.*—Quantity per inflorescence: About 22. Length: About 5 mm. Width: About 2 mm. Shape: Ligulate. Apex: Acute. Base: Truncate. Margin: Entire. Texture, upper surface: Smooth, waxy. Texture, lower surface: Pubescent. Color, upper surface: Close to 146A. Color, lower surface: Close to 147A.

*Peduncle.*—Length: First peduncle: About 3.2 cm. Fourth peduncle: About 5 cm. Seventh peduncle: About 6.8 cm. Diameter: About 1 mm. Strength: Strong. Aspect: About 40 to 45° from vertical. Texture: Pubescent. Color: Close to 146A.

*Reproductive organs.*—Gynoecium: Present on ray florets.

*Seed/fruit.*—Seed and fruit production has not been observed.

Disease/pest resistance: Plants of the new *Chrysanthemum* have not been shown to be resistant to pathogens and pests common to *Chrysanthemums*.

Garden performance: Plants of the new *Chrysanthemum* have been observed to be tolerant to rain, wind and temperatures ranging from 0 to more than 38° C.

It is claimed:

1. A new and distinct cultivar of *Chrysanthemum* plant named 'Rosy Yovictoria', as illustrated and described.

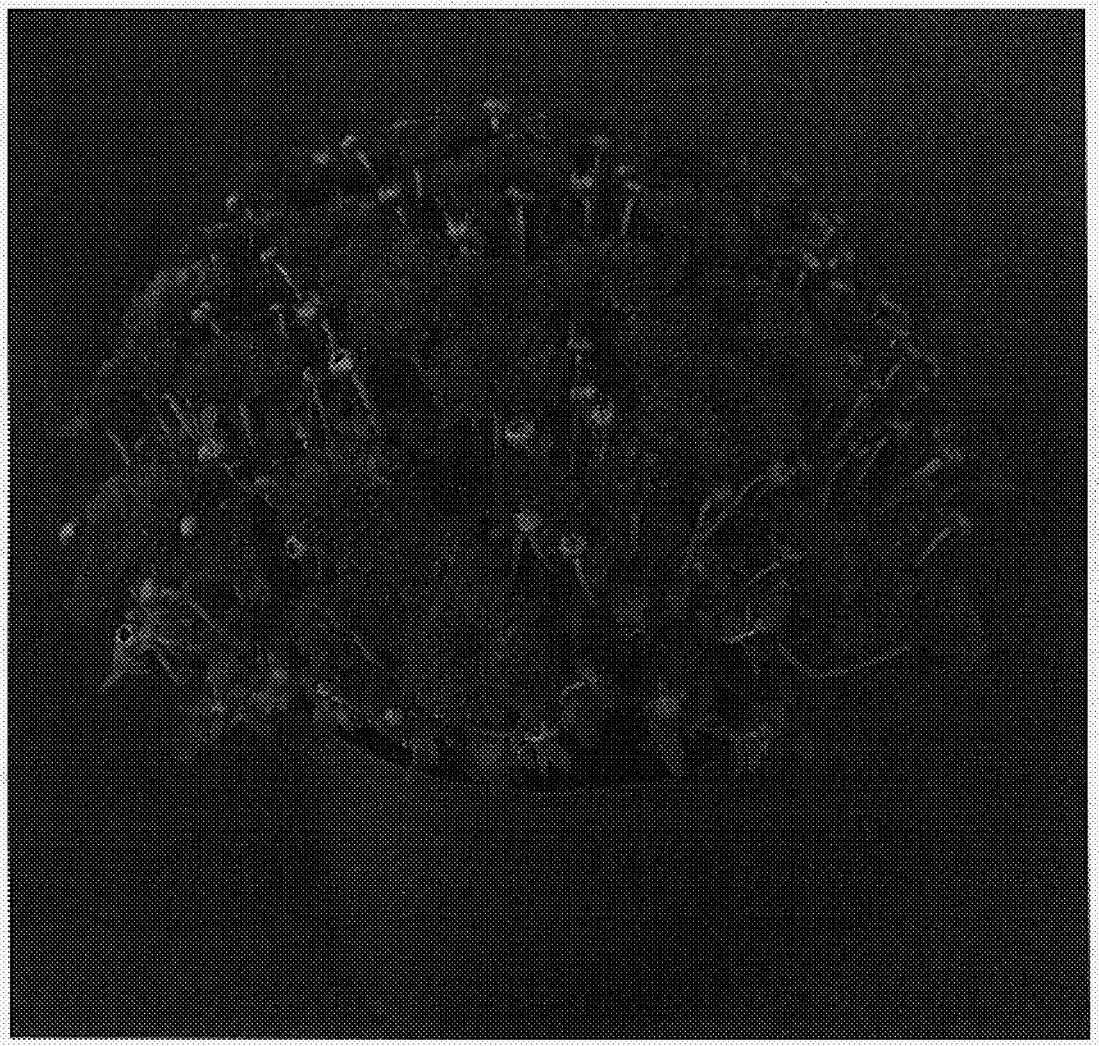

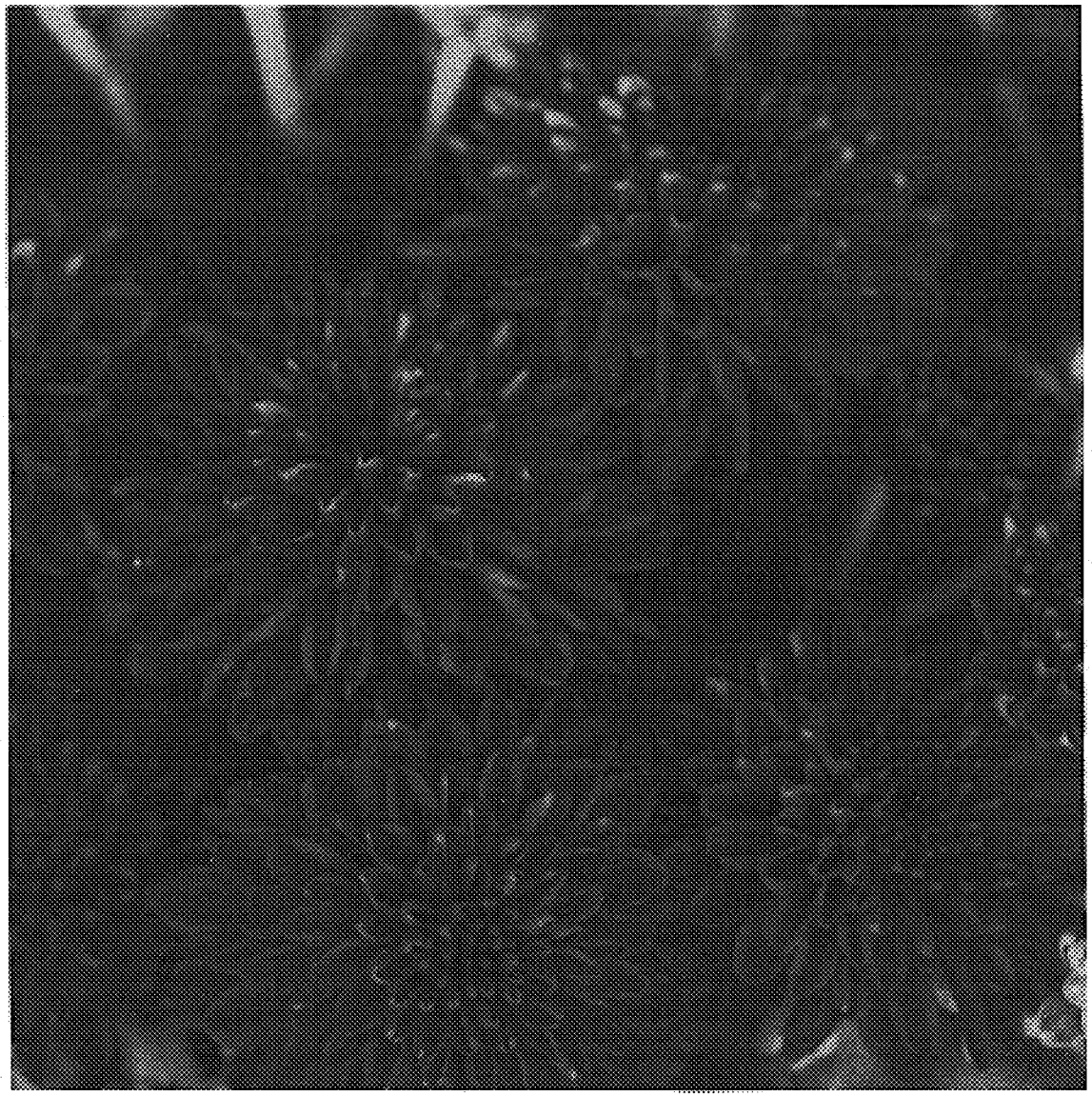

* * * * *